(12) United States Patent
Kitamura et al.

(10) Patent No.: US 7,432,390 B2
(45) Date of Patent: Oct. 7, 2008

(54) PRODUCTION OF CARBOXYLIC ACIDS OR CARBOXYLIC ACID ESTERS

(75) Inventors: Mitsuharu Kitamura, Okayama (JP); Kinji Kato, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/370,918

(22) Filed: Mar. 9, 2006

(65) Prior Publication Data

US 2006/0205970 A1  Sep. 14, 2006

(30) Foreign Application Priority Data

Mar. 10, 2005  (JP) .............................. 2005-066573

(51) Int. Cl.
*C07C 67/36* (2006.01)
(52) U.S. Cl. .................. 560/114; 560/76; 562/400; 562/423; 562/498
(58) Field of Classification Search ................ 560/114, 560/76; 562/400, 423, 498
See application file for complete search history.

(56) References Cited

U.S. PATENT DOCUMENTS 3,005,846 A   10/1961  Friedman et al.
4,452,999 A *  6/1984  Besecke et al. ............ 560/233
4,661,296 A *  4/1987  Grote et al. ................ 554/130
5,463,095 A   10/1995  Shiokawa et al.
6,194,602 B1 *  2/2001  Karas ......................... 560/247

FOREIGN PATENT DOCUMENTS

EP   0 347 621   12/1989

OTHER PUBLICATIONS

European Search Report, for Application No. EP 06 11 0648, dated Jun. 26, 2006.

* cited by examiner

*Primary Examiner*—Yvonne Eyler
*Assistant Examiner*—Sudhakar Katakam
(74) *Attorney, Agent, or Firm*—Antonelli, Terry, Stout & Kraus, LLP.

(57) ABSTRACT

In the production of carboxylic acid or carboxylic acid ester, a reaction product containing the carboxylic acid or carboxylic acid ester which has been produced by the reaction of an olefin, carbon monoxide, and water or an alcohol in the presence of HF is heat-treated in the presence of an acid catalyst and an acid adsorbent. By the heat treatment, the contamination of the carboxylic acid or carboxylic acid ester with HF and/or fluorine compounds such as acyl fluorides can be prevented, to enable the stable production of a high quality and high purity carboxylic acid or carboxylic acid ester without causing troubles such as corrosion of apparatus.

9 Claims, No Drawings

PRODUCTION OF CARBOXYLIC ACIDS OR CARBOXYLIC ACID ESTERS

BACKGROUND OF THE INVENTION

1. Field of the Invention

The present invention relates to a method of producing carboxylic acids or carboxylic acid esters, more specifically, relates to a method of producing carboxylic acids or carboxylic acid esters having their contents of fluorine compounds (inorganic fluorine compounds and organic fluorine compounds) reduced.

2. Description of the Prior Art

As one of the methods for producing carboxylic acid esters from olefins in the presence of a strong acid catalyst, Koch reaction has been known, in which an olefin is carbonylated with carbon monoxide to form an acyl compound, the acyl compound is converted into a carboxylic acid by the reaction with water, and the carboxylic acid is then converted into an ester by the reaction with an alcohol.

The productions of pivalic acid from isobutene and C6-C11 carboxylic acids from C5-C10 olefins are known as the examples of Koch reaction for producing secondary or tertiary carboxylic acids.

As the catalyst for the production of carboxylic acid by Koch reaction, an inorganic acid such as sulfuric acid, HF and phosphorous acid is used singly or in the form such as $HF \cdot SbF_5$ and $H_3PO_4 \cdot BF_3$ in combination with $BF_3$ or $SbF_5$. In the later stage of the reaction, water is added to separate the product and the catalyst. Therefore, this method involves a problem that the catalyst diluted with water should be recovered and regenerated.

The esterification of a carboxylic acid with an alcohol is conducted while removing water in the presence of an acid catalyst, for example, an inorganic acid such as sulfuric acid, HF, phosphorous acid and hydrochloric acid; an alkylsulfonic acid such as methanesulfonic acid and trifluoromethanesulfonic acid; an arylsulfonic acid such as p-toluenesulfonic acid; a metal alkoxide such as tetrabutoxytitanium; or a Lewis acid such as boron fluoride etherate. Since the rate of esterification is low in case of esterifying a branched secondary or tertiary carboxylic acid, the esterification of such a carboxylic acid involves difficulty for its industrial use.

To solve such a problem, proposed is a method in which an olefin is carbonylated into an acyl fluoride in the presence of HF as an acid catalyst, and then the acyl fluoride is esterified with an alcohol in the presence of HF (for example, U.S. Pat. No. 5,463,095). The proposed method is excellent because the recovery of catalyst is easy, and the carbonylation and esterification proceed quite easily. However, the patent describes and considers nothing about the stoichiometric control of the acyl fluoride and alcohol and the reduction of the content of organic fluorine compounds in the product.

As a result of research in view of solving the problems in the above known methods, the inventors have found that a carboxylic acid ester can be efficiently produced from an olefin, carbon monoxide and an alcohol, and filed a patent application on the basis of this finding (JP 9-328451A). In the proposed method, the esterification in the presence of HF catalyst is conducted by controlling the addition amount of the alcohol, thereby regulating the content of residual acyl fluoride in the produced ester within the specific range, and preventing the formation of water due to the dehydration of non-reacted alcohol. After removing HF catalyst, the residual acyl fluoride is esterified with an alcohol. Since the formation of water which is difficult to separate from HF catalyst is prevented, the high performance HF catalyst can be recycled for reuse. In addition, the carboxylic acid ester having its content of fluorine impurities reduced can be easily and stably produced. Therefore, the proposed method is industrially advantageous. However, it was found that high boiling products were decomposed under heating during the purification of the carboxylic acid ester by distillation, resulting in the contamination of the carboxylic acid ester with fluorine impurities such as HF and acyl fluoride. The fluorine impurities reduce the purity of the products and cause troubles such as corrosion of apparatus.

SUMMARY OF THE INVENTION

The present invention provides an industrially advantageous method of producing purified carboxylic acids or carboxylic acid esters having their contents of fluorine compounds extremely reduced.

As a result of intensive research in view of solving the above problems, the inventors have found that the content of organic fluorine compounds in crude carboxylic acids or carboxylic acid esters, which are produced by the reaction of an olefin, carbon monoxide, and water or alcohol in the presence of HF, is reduced by heat-treating the crude products in the presence of an acid catalyst. It has been also found that HF generated by the decomposition of organic fluorine compounds is present in a slight amount in the mother liquor of such a heat treatment, thereby likely to contaminating the carboxylic acid or carboxylic acid ester. After a further research in view of these findings, it has been found that carboxylic acids and carboxylic acid esters having their contents of fluorine compounds extremely reduced can be obtained by heat-treating the crude carboxylic acids or carboxylic acid esters in the presence of an acid adsorbent together with the acid catalyst in an industrially advantageous manner without causing troubles such as corrosion of apparatus. The present invention is based on these findings.

Thus, the present invention relates to a method of producing a carboxylic acid or carboxylic acid ester, which comprises a step of producing a reaction product containing the carboxylic acid or carboxylic acid ester by a reaction of an olefin, carbon monoxide, and water or an alcohol in the presence of HF, and a step of heat-treating at least a part of the reaction product in the presence of an acid catalyst and an acid adsorbent.

DETAILED DESCRIPTION OF THE INVENTION

In the present invention, at least a part of the reaction product containing a carboxylic acid or carboxylic acid ester which has been obtained by the reaction of an olefin, carbon monoxide, and water or an alcohol in the presence of HF is heat-treated in the presence of an acid catalyst and an acid adsorbent. The conditions of the reaction for producing such a reaction product are not critical in the present invention. Any of the reaction products containing a carboxylic acid or carboxylic acid ester obtained by the reaction under known conditions can be used as the starting material for the method of the present invention.

Preferably, the crude carboxylic acid or carboxylic acid ester obtained by removing HF from the reaction product by distillation is subjected to the heat treatment. The resultant crude carboxylic acid or carboxylic acid ester as obtained may be heat-treated in the presence of the acid catalyst and the acid adsorbent. Alternatively, the heat treatment may be conducted after removing low boiling component and high boiling component from the crude carboxylic acid or carboxylic acid ester by a simple distillation. In addition, the heat treatment may be conducted after reducing the content of fluorine compounds by allowing the residual carboxylic fluoride in the crude carboxylic acid or carboxylic acid ester to react with water or an alcohol in the presence of a newly added esterification catalyst. The crude carboxylic acid or carboxylic acid ester having a higher content of fluorine compounds may be heat-treated without such a treatment for reducing the content of fluorine compounds.

The olefin is selected from aliphatic chain olefins and alicyclic olefins according to the intended properties of the carboxylic acid and carboxylic acid ester, although not limited thereto. Examples thereof include propylene, butylene, isobutylene, pentene, hexene, octene, cyclohexene, cyclododecene, dihydrodicyclopentadiene(DHDCPD), and tricyclododecene.

The alcohol is selected from chain or alicyclic monohydric or polyhydric alcohols according to the intended properties of the carboxylic acid and carboxylic acid ester, although not limited thereto. Examples thereof include methanol, ethanol, propanol, isopropanol, butanol, pentanol, hexanol, heptanol, octanol, ethylene glycol, propylene glycol, glycerol, sorbitol, neopentyl glycol, trimethylolethane, trimethylolpropane, and pentaerythritol.

Examples of the acid catalyst include liquid acids such as sulfuric acid and solid acids such as activated clay, acid clay, faujasite, X-type zeolite, Y-type zeolite, mordenite, silica—alumina, and strongly acidic ion exchange resins, with solid acids being preferred because of easiness of removal. These acid catalysts may be used alone or in combination of two or more. The amount of the acid catalyst to be added is preferably from 0.005 to 0.1, more preferably from 0.01 to 0.05 when expressed by the weight ratio of acid catalyst/carboxylic acid or carboxylic acid ester. Within the above range, the organic fluorine compounds are sufficiently decomposed, the volumetric efficiency of apparatus is good, and the acid catalyst can be separated cost-effectively. The use of a large amount exceeding a weight ratio of 0.1 creates substantially no additional increase in the decomposition of organic fluorine compounds.

Examples of the acid adsorbents include magnesium oxide, aluminum hydroxide, magnesium hydroxide, basic aluminum, magnesium silicate, synthetic aluminum silicate, and basic anion exchange resins. These acid adsorbents may be used alone or in combination of two or more. The amount of the acid adsorbent to be added is preferably from 0.0005 to 0.01, more preferably from 0.001 to 0.005 when expressed by the weight ratio of acid adsorbent/carboxylic acid or carboxylic acid ester. Within the above range, HF is sufficiently adsorbed onto the acid adsorbent, and the acid adsorbent can be separated cost-effectively. The use of a large amount exceeding a weight ratio of 0.01 creates substantially no additional increase in the adsorption of HF.

The heat treatment is conducted preferably at 120 to 250° C., more preferably at 150 to 200° C. The heat-treating time of about 1 to 5 h is sufficient for reducing the content of fluorine compounds. If the heat-treating temperature is within the above range, the organic fluorine compounds are efficiently decomposed without causing the decomposition of the carboxylic acid or carboxylic acid ester. A heat-treating temperature exceeding 250° C. produces substantially no additional increase in the decomposition of organic fluorine compounds.

After the heat treatment, the acid catalyst and the acid adsorbent are removed from the treated liquid by solid-liquid separation, etc. The resultant liquid is then distilled by a known method to obtain a purified carboxylic acid or carboxylic acid ester having a low content of fluorine compounds. According to the present invention, the total fluorine content (content of fluorine derived from inorganic fluorine compounds and organic fluorine compounds) of the purified carboxylic acid or carboxylic acid ester can be reduced to preferably as low as 5 ppm or lower, more preferably as low as 2 ppm or lower, and still more preferably as low as 1 ppm or lower.

The present invention will be described in more detail with reference to the following examples. However, it should be noted that the following examples are merely illustrative and the scope of the present invention is not limited thereto.

The content of fluorine was determined by the following method.

Fluorine Analysis

A sample was decomposed by combustion using an oxyhydrogen flame halogen analyzer. The decomposed products were absorbed into distilled water. Then, $F^-$ in the resultant aqueous solution was quantitatively analyzed using ion electrodes and the results were calibrated to determined the total fluorine content of the sample. After washing the same sample with water to fully remove inorganic compounds, the same analysis was repeated to determine the content of fluorine derived from organic fluorine compounds (organic fluorine content). The content of fluorine derived from inorganic fluorine compounds (inorganic fluorine content) was calculated from the following equation:

inorganic fluorine content=total fluorine content−organic fluorine content.

SYNTHESIS EXAMPLE 1

(1) Carbonylation

The inner atmosphere of a 10-L stainless autoclave equipped with a stirrer, three upper inlet nozzles, one bottom discharge nozzle and a jacket for regulating the inner temperature was replaced by carbon monoxide. After charging 3 kg (150 mol) of hydrogen fluoride, carbon monoxide was introduced into the autoclave until reaching 2 MPa.

The carbonylation was conducted by feeding 1,222 g (10 mol) of 1-octene into the autoclave over about 60 min from its upper portion while maintaining the reaction temperature at −20° C. and reaction pressure at 2 MPa. The stirring was further continued for about 15 min until carbon monoxide was no longer absorbed. The amount of carbon monoxide absorbed was 7.2 mol.

(2) Esterification

By reducing the pressure to atmospheric pressure, non-reacted carbon monoxide was purged. Then, the temperature was raised to 0° C. to proceed the esterification for one hour under stirring while feeding 224 g (7.0 mol) of methanol into the autoclave from its upper portion over about 20 min. After removing the hydrogen fluoride catalyst by distillation, the resultant reaction liquid was washed with 2 wt % NaOH aqueous solution for neutralization. The analysis of the reaction liquid showed the formation of 6 kinds of ester isomers, and the content of acyl fluorides was 2.0% by weight based on the total weight of the ester isomers.

To 800 g of esters obtained above (acyl fluoride content: 0.72 mol) in a 2-L stainless vessel with cover equipped with a reflux condenser, a 98% sulfuric acid was added under stirring in an amount of 0.2% by weight of the esters, and the temperature was raised to 70° C. After adding 93 g (2.9 mol) of methanol, the resultant mixture was stirred for 30 min. The residual acyl fluorides were completely esterified. The total fluorine content of the reaction liquid was 18 ppm. The organic fluorine content (mainly derived from high boiling products) was 17 ppm and the inorganic fluorine content (mainly derived from HF) was 1 ppm.

(3) Preparation of Crude Carboxylic Acid Ester

The reaction liquid was washed with a 2 wt % NaOH aqueous solution for neutralization, and then, purified by a distillation column with five theoretical plates, to collect 730 g of main fraction. The total fluorine content of the main fraction was 19 ppm. The total fluorine content was increased during the distillation because of the inclusion of products which were resulted from the thermal decomposition of organic fluorine compounds in the high boiling products. The main fraction (crude carboxylic acid ester) had an inorganic content of 4 ppm and an organic fluorine content of 15 ppm.

EXAMPLE 1

Into a 300-mL four-necked flask equipped with a mechanical stirrer, a nitrogen inlet nozzle, a thermometer and a gas discharge line, 100 g of the crude carboxylic acid ester prepared in Synthesis Example 1, 2.0 g of activated clay (acid catalyst), 0.2 g of aluminum hydroxide gel (acid adsorbent) "Kyowaad 200 B" available from Kyowa Chemical Industry Co., Ltd. ware charged. The contents were heated to 180° C. under stirring in nitrogen flow. No HF was found in the gas from the gas discharge line when examined by a pH test paper. The stirring was continued for 3 h under the same conditions, and then, the temperature was lowered to room temperature. After cooling, activated clay and aluminum hydroxide gel were separated out by filtration. The filtrate was analyzed for the fluorine contents. The inorganic fluorine content was less than 1 ppm and the organic fluorine content was 1 ppm. The whole of the filtrate was purified by a distillation column with 20 theoretical plates, to obtain 92 g of purified carboxylic acid ester. Each of the inorganic fluorine content and organic fluorine content was 1 ppm or less.

COMPARATIVE EXAMPLE 1

The same heat treatment as in Example 1 was repeated except for omitting the use of the acid adsorbent (aluminum hydroxide gel). A large amount of HF was found in the gas from the gas discharge line. The liquid after removing activated clay had an inorganic fluorine content of 4 ppm and an organic fluorine content of 1 ppm. The obtained carboxylic acid ester was contaminated with HF because no acid adsorbent was used.

COMPARATIVE EXAMPLE 2

The same heat treatment as in Example 1 was repeated except for using 2.0 g of aluminum hydroxide gel and omitting the use of the acid catalyst (activated clay). No HF was found in the gas from the gas discharge line. The liquid after removing aluminum hydroxide gel had an inorganic fluorine content of less than 1 ppm and an organic fluorine content of 15 ppm. The organic fluorine compounds were not decomposed because the use of the acid catalyst was omitted.

EXAMPLE 2

The same heat treatment as in Example 1 was repeated except for changing the treating temperature to 150° C. No HF was found in the gas from the gas discharge line. The liquid after removing activated clay and aluminum hydroxide gel had an inorganic fluorine content of less than 1 ppm and an organic fluorine content of 2 ppm. The whole liquid was purified by a distillation column with 20 theoretical plates, to obtain 92 g of purified carboxylic acid ester. The inorganic fluorine content was less than 1 ppm and the organic fluorine content was 1 ppm.

EXAMPLE 3

The same heat treatment as in Example 1 was repeated except for using 1.0 g of activated clay. No HF was found in the gas from the gas discharge line. The liquid after removing activated clay and aluminum hydroxide gel had an inorganic fluorine content of less than 1 ppm and an organic fluorine content of 2 ppm. The whole liquid was purified by a distillation column with 20 theoretical plates, to obtain 94 g of purified carboxylic acid ester. The inorganic fluorine content was less than 1 ppm and the organic fluorine content was 1 ppm.

EXAMPLE 4

The same heat treatment as in Example 1 was repeated except for using 0.1 g of aluminum hydroxide gel. No HF was found in the gas from the gas discharge line. The liquid after removing activated clay and aluminum hydroxide gel had an inorganic fluorine content of less than 1 ppm and an organic fluorine content of 1 ppm. The whole liquid was purified by a distillation column with 20 theoretical plates, to obtain 93 g of purified carboxylic acid ester. Each of the inorganic fluorine content and organic fluorine content was 1 ppm or less.

SYNTHESIS EXAMPLE 2

(1) Carbonylation

The inner atmosphere of a 500-mL stainless autoclave equipped with a stirrer, three upper inlet nozzles, one bottom discharge nozzle and a jacket for regulating the inner temperature was replaced by carbon monoxide. After charging 150 g (7.5 mol) of hydrogen fluoride, the inner temperature was adjusted to 30° C. and carbon monoxide was introduced into the autoclave until reaching 2 MPa.

The carbonylation was conducted by feeding 224 g of a mixture, DHDCPD/ethanol/n-heptane=1/0.10/0.68 by weight (1/0.30/0.91 by mole), into the autoclave from its upper portion while maintaining the reaction temperature at 30° C. and reaction pressure at 2 MPa, to produce acyl fluoride corresponding to DHDCPD. After completing the feed of DHDCPD, the stirring was continued for about 10 min until carbon monoxide was no longer absorbed. The amount of carbon monoxide absorbed was 7.1 mol.

(2) Esterification

Then, ethanol was fed into the autoclave from its upper portion in an amount of 0.7 time the amount of DHDCPD while maintaining the reaction temperature at 0° C., to allow the esterification to proceed for one hour under stirring.

The reaction product liquid discharged from the bottom of the autoclave was poured into an iced water. After separated into an oil phase and a water phase, the oil phase was washed twice with 100 mL of a 2 wt % NaOH aqueous solution, further washed twice with 100 mL of distilled water, and then, dried over 10 g of anhydrous sodium sulfate. The dried oil phase was gas chromatographically analyzed by internal standard method. The results showed that ethyl tricyclo [5.2.1.0$^{2,6}$]decane-2-carboxylate (TCDCE) was produced in a yield of 63.1% based on DHDCPD, and TCDCE consisted of exo-tricyclo[5.2.1.0$^{2,6}$]decane-endo-2-carboxylic acid ester (referred to as "endo TCDCE" according to the steric conformation of ester group) and endo-tricyclo[5.2.1.0$^{2,6}$] decane-exo-2-carboxylic acid ester (exo TCDCE) in a ratio (endo TCDCE/exo TCDCE) of 0.45.

(3) Preparation of Crude Carboxylic Acid Ester

The oil phase was purified by a distillation column with five theoretical plates, to collect 110 g of main fraction. The main fraction (crude carboxylic acid ester) had an inorganic content of 50 ppm and an organic fluorine content of 870 ppm.

EXAMPLE 5

The same procedure as in Example 1 was repeated except for using the crude carboxylic acid ester prepared in Synthesis Example 2. No HF was found in the gas from the gas discharge line. The liquid after removing activated clay and aluminum hydroxide gel had an inorganic fluorine content of less than 1 ppm and an organic fluorine content of 4 ppm. The whole liquid was purified by a distillation column with 20 theoretical plates, to obtain 92 g of purified carboxylic acid ester. The inorganic fluorine content was less than 1 ppm and the organic fluorine content was 3 ppm. The endo TCDCE/exo TCDCE ratio was 0.45.

SYNTHESIS EXAMPLE 3

(1) Carbonylation

The inner atmosphere of a 1-L stainless autoclave equipped with a stirrer, three upper inlet nozzles, one bottom discharge nozzle and a jacket for regulating the inner temperature was replaced by carbon monoxide. After charging 256 g (12.8 mol) of hydrogen fluoride, the inner temperature was adjusted to 30° C. and carbon monoxide was introduced into the autoclave until reaching 2 MPa.

The carbonylation was conducted by feeding 358 g of a n-heptane solution dissolving 214.7 g (1.60 mol) of DHDCPD into the autoclave from its upper portion while maintaining the reaction temperature at 30° C. and reaction pressure at 2 MPa. After completing the feed of DHDCPD, the stirring was continued for about 10 min until carbon monoxide was no longer absorbed.

A portion sampled from the obtained reaction product liquid was poured into an iced water. After separated into an oil phase and a water phase, the oil phase was neutralized and washed with water. The resultant oil phase was chromatographically analyzed. The ratio of endo isomer/exo isomer was 0.53.

Then, the reaction temperature was raised to 55° C. while maintaining the reaction pressure at 2 MPa, and the autoclave was maintained at such conditions for 8 h, to conduct the isomerization. Thereafter, the reaction temperature was lowered to –10° C., and 28.8 g (1.60 mol) of water was added to the autoclave from its upper portion, to conduct the hydrolysis for one hour under stirring.

The reaction product liquid discharged from the bottom of the autoclave was poured into an iced water. After separated into an oil phase and a water phase, the oil phase was washed twice with 100 mL of a 2 wt % NaOH aqueous solution, further washed twice with 100 mL of distilled water, and then, dried over 10 g of anhydrous sodium sulfate. The dried oil phase was gas chromatographically analyzed by internal standard method. The results showed that tricyclo[5.2.1.0$^{2,6}$] decane-2-carboxylic acid (TCDA) was produced in a yield of 51.5% based on DHDCPD in an endo isomer/exo isomer of 10.3.

(2) Preparation of Crude Carboxylic Acid

The oil phase was fractionated by a fractionating column with 20 theoretical plates, to obtain a main fraction containing 90.24% by weight of endo TCDA and 8.76% by weight of exo TCDA (endo isomer/exo isomer=10.3) in a distillation yield of 86.6%. The main fraction (crude carboxylic acid) had an inorganic content of 30 ppm and an organic fluorine content of 550 ppm. The isomer ratio was not changed by the distillation.

EXAMPLE 6

The same procedure as in Example 1 was repeated except for using the crude carboxylic acid prepared in Synthesis Example 3 in place of the crude carboxylic acid ester. No HF was found in the gas from the gas discharge line. The liquid after removing activated clay and aluminum hydroxide gel had an inorganic fluorine content of less than 1 ppm and an organic fluorine content of 3 ppm. The whole liquid was purified by a distillation column with 20 theoretical plates, to obtain 91 g of purified carboxylic acid ester. The inorganic fluorine content was less than 1 ppm and the organic fluorine content was 2 ppm. The endo isomer/exo isomer ratio was 10.3.

By purifying a carboxylic acid or a carboxylic acid ester in the manner of the present invention, the content of fluorine compounds therein is extremely reduced. Therefore, a carboxylic acid or a carboxylic acid ester having a low content of fluorine compounds can be produced in industrially advantageous manner without causing troubles such as corrosion of apparatus. Thus, the present invention is of industrially great advantage.

What is claimed is:

1. A method of producing a carboxylic acid or carboxylic acid ester, which comprises a step of producing a crude reaction product containing the carboxylic acid or carboxylic acid ester by a reaction of an olefin, carbon monoxide, and water or an alcohol in the presence of HF catalyst, and a step of heat-treating at least a part of the crude reaction product, at a temperature of 150 to 200° C. for 1 to 5 hours, in the presence of a solid acid as an acid catalyst, that acts as a catalyst in decomposition of organic fluorine compounds, and an acid adsorbent, wherein an amount of the solid acid used is from 0.005 to 0.1 part by weight per one part by weight of the carboxylic acid or carboxylic acid ester, and the amount of the acid adsorbent used is from 0.001 to 0.005 part by weight per one part by weight of the carboxylic acid or carboxylic acid ester, and the product obtained by the heat-treating is subjected to distillation.

2. The method according to claim 1, wherein the acid catalyst is at least one catalyst selected from the group consisting of activated clay, acid clay, faujasite, X-type zeolite, Y-type zeolite, mordenite, silica-alumina, and strongly acidic ion exchange resins.

3. The method according to claim 1, wherein the acid adsorbent is at least one adsorbent selected from the group consisting of magnesium oxide, aluminum hydroxide, magnesium hydroxide, basic aluminum, magnesium silicate, synthetic aluminum silicate, and basic anion exchange resins.

4. The method according to claim 1, wherein said amount of the acid catalyst is 0.01 to 0.05 part by weight per one part by weight of the carboxylic acid or carboxylic acid ester.

5. The method according to claim 1, including the further step, after said step of heat-treating, of removing said acid catalyst and said acid adsorbent from the reaction product having been treated in the heat-treating step.

6. The method according to claim 5, wherein said removing is performed by solid-liquid separation.

7. The method according to claim 1, wherein the step of heat-treating is a separate step from the step of producing the crude reaction product.

8. The method according to claim 1, wherein the acid adsorbent adsorbs HF.

9. The method according to claim 8, wherein the heat-treatment in the presence of the acid catalyst and the acid adsorbent purifies the crude reaction product containing the carboxylic acid or carboxylic acid ester.

* * * * *